United States Patent [19]

Van Sickle et al.

[11] Patent Number: 5,210,279

[45] Date of Patent: May 11, 1993

[54] PROCESS FOR MANUFACTURING AROMATIC DIACETATES

[75] Inventors: Dale E. Van Sickle; Brad W. Overturf, both of Kingsport, Tenn.

[73] Assignee: Eastman Kodak Company, Rochester, N.Y.

[21] Appl. No.: 551,662

[22] Filed: Jul. 12, 1990

Related U.S. Application Data

[63] Continuation of Ser. No. 456,444, Dec. 26, 1989, abandoned, which is a continuation of Ser. No. 190,296, May 4, 1989, abandoned, which is a continuation-in-part of Ser. No. 50,805, May 18, 1987, abandoned.

[51] Int. Cl.$^5$ ............................................. C07C 69/017
[52] U.S. Cl. ..................................... 560/139; 560/141; 560/144
[58] Field of Search ......................... 560/139, 141, 144

[56] References Cited

U.S. PATENT DOCUMENTS 2,799,698  7/1957  Taves .................................. 560/144
3,028,410  4/1962  Zimmer, Jr. ...................... 568/565 X

*Primary Examiner*—José G. Dees
*Assistant Examiner*—Samuel Barts
*Attorney, Agent, or Firm*—J. Frederick Thomsen; William P. Heath, Jr.

[57] ABSTRACT

A continuous process for the production of diacetate derivatives of aromatic compounds, comprising feeding at any convenient temperature an oxygen-containing gas and feedstock comprising a diisopropyl ring substituted aromatic compound and the recycled monoisopropyl-monoacetate derivative thereof, to an oxidizer operated, for example, at from about 10° C. to about 150° C. and oxygen partial pressures of from about 0.05 to 10 atmospheres to form an oxidizer product comprising the mono- and dihydroperoxides of the feedstock, feeding the oxidizer product to a rearrangement-esterification zone containing acetic anhydride at from about 0° C. to 150° C. to form an ester product comprising the diacetate and monoisopropyl-monoacetate derivatives of the feedstock, distilling the ester product to separate the diacetate and monoisopropyl-monoacetate derivatives, and recycling the monoisopropyl-monoacetate derivative back to the oxidizer.

5 Claims, No Drawings

PROCESS FOR MANUFACTURING AROMATIC DIACETATES

This is a continuation of copending application Ser. No. 07/456,444 filed on Dec. 26, 1989, abandoned which is a continuation of Ser. No. 07/190,296 filed May 4, 1988, abandoned which is a continuation-in-part of Ser. No. 07/50,805 filed May 18, 1987 -abandoned.

DESCRIPTION

This invention concerns a process for the manufacture of diacetate esters of aromatic diols which simplifies the reaction equipment and allows non-complex distillative separation of product from intermediate recycle materials and by-products.

Diacetate esters of aromatic diols such as hydroquinone, resorcinol, 2,6-naphthalenediol and 4,4'-biphenyldiol have utility in the manufacture of polyesters, such as those disclosed in U.S. Pat. No. 4,318,814, which are useful in high modulus fibers or other formed articles.

Previously, diacetate esters of aromatic diols such as 1,4-phenylene-bis(acetate) (hydroquinone diacetate) and 4,4'-biphenylene diacetate have been prepared by batch acetylation of the isolated aromatic diol, e.g., hydroquinone, according to well-known procedures. The isolated hydroquinone typically is produced by the "Hock" acid-catalyzed rearrangement of the dihydroperoxide of p-diisopropylbenzene (p-DIPB). This process requires careful, elaborate and costly separation of the monohydroperoxide and dihydroperoxide of p-DIPB, both of which result from the oxidation of p-DIPB. Such separation is necessary prior to the rearrangement of the dihydroperoxide to hydroquinone and is quite tedious since the desired p-DIPB dihydroperoxide is present in only about 1/20 the concentration of the monohydroperoxide. The thermal instability of the hydroperoxides precludes distillative separation, thus necessitating special extraction or crystallization procedures. Moreover, deposition of the unstable p-DIPB dihydroperoxide crystals from purification solvents represents a serious drawback to any process requiring p-DIPB dihydroperoxide isolation.

In a process wherein the monohydroperoxide is not separated from the dihydroperoxide prior to the Hock rearrangement, p-isopropylphenol is produced. However, p-isopropylphenol cannot be recycled to the p-DIPB oxidizer since it inhibits the oxidation of p-DIPB to the monohydroperoxide and the monohydroperoxide to the dihydroperoxide. Thus, the large amount of p-isopropylphenol which would be produced by the Hock rearrangement and which cannot be recycled would result in a drastic loss of process efficiency and yield to hydroquinone diacetate.

We have discovered that the rearrangement of hydroperoxides of dialkyl aromatic compounds such as diisopropylbenzene, diisopropylnaphthalene and diisopropylbiphenyl compounds, especially p-DIPB, can be carried out efficiently in acetic anhydride solvent and that the resulting aromatic acetates and unconverted reactants can be conveniently and economically separated by distillation. Furthermore, the intermediate mono-acetate compound, i.e., isopropyl aromatic acetate such as p-isopropylphenylacetate (p-IPPAc), resulting from rearrangement and esterification of the monohydroperoxide, can be returned to the oxidation reactor and oxidized further to the hydroperoxide of the monoacetate along with new or recycled p-DIPB reactant. The isopropyl aromatic acetate compound is readily oxidized to its hydroperoxide which then may be converted to the aromatic diacetate by Hock rearrangement in the presence of acetic anhydride.

Our invention therefore concerns a continuous process for the preparation of diacetate esters of aromatic diols which comprises the steps of:

(1) contacting in an oxidation zone a feedstock comprising a diisopropyl aromatic compound and recycle isopropyl aromatic acetate with an oxygen-containing gas under hydroperoxide forming conditions of temperature and pressure to form a reaction mixture comprised of the mono- and di-hydroperoxides of the feedstock;

(2) contacting in a rearrangement-esterification zone the reaction mixture formed in the oxidation zone with an acidic rearrangement catalyst and acetic anhydride under rearrangement-esterification conditions of temperature and pressure to form an ester mixture comprising the diacetate of the corresponding aromatic diol and the isopropyl aromatic acetate;

(3) submitting the ester mixture obtained from the rearrangement-esterification zone to distillation to separate the diacetate compound from the acetate compound; and (4) recycling the acetate compound to the oxidation zone.

Oxidation step (1) is carried out in accordance with known procedures such as, for example, the procedures described in U.S. Pat. No. 3,360,570. Generally, this step involves contacting a mixture comprising both fresh and recycle diisopropyl aromatic compound and recycle isopropyl aromatic acetate with a gas containing molecular oxygen which normally is air although oxygen or oxygen-enriched air may be used. The oxidation is carried out in the liquid phase by intimately contacting according to known means the feedstock with the oxygen-containing gas. The temperature within the oxidation zone can vary over a wide range, e.g., from about 10° to 150° C. Normally, the oxidation temperature will be in the range of about 50° to 120° C., preferably in the range of about 70° to 100° C. The pressure within the oxidation zone also can be varied substantially, e.g., oxygen partial pressures over the range of from about 0.05 to 10 atmospheres. A more typical oxygen partial pressure range is from about 0.2 to 5 atmospheres with the preferred range being from about 0.2 to 3.0 atmospheres.

The oxidation step of the process requires the presence of a free radical initiator such as 1,1'-azobis(cyclohexanecarbonitrile), 2,2'-azobis(2-methylpropionitrile), 2-t-butylazo-2-cyanopropane and the like and peroxides such as the mono- and di-hydroperoxides of the feedstock, benzoyl peroxide, di-t-butyl peroxide, etc. The amount of initiator can be varied over a wide range depending on the oxidation rate and "kinetic chain length" desired and the particular initiator employed. Generally, molar ratios of initiator diisopropyl aromatic compound in the range of 0.005 to 0.1 may be used.

In a preferred mode of continuous operation, one or more aromatic alkyl compounds such as a diisopropyl aromatic compound is being continuously oxidized to a hydroperoxide in a columnar, back-mixed oxidizer and a portion of the reaction mixture formed in the oxidizer is continuously removed. Thus, hydroperoxide is always present in the oxidation zone to sustain the oxidation of the feedstock and the use of an extraneous free radical initiator is avoided.

Normally, the oxidation is carried out in the presence of a weak base which functions to neutralize any acids formed by the process since such acids act as catalysts for the hydroperoxide rearrangement to produce phenols which retard substantially the oxidation reaction. Examples of suitable bases include the alkali metal bicarbonates, e.g., sodium and potassium bicarbonate, the alkaline earth metal hydroxides, e.g., magnesium, calcium and barium hydroxide.

The diisopropyl aromatic compound which is used as the raw material in the oxidation zone may be any compound wherein the aromatic nucleus, i.e., the aromatic ring or rings, contain from 6 to 14 carbon atoms. Examples of the diisopropyl aromatic compounds which may be used in our process include the diisopropylbenzenes, e.g., 1,3- and 1,4-diisopropylbenzene; the diisopropylnaphthalenes, e.g., 2,6- and 2,7-diisopropylnaphthalene; and the diisopropylbiphenyls, e.g., 4,4'-diisopropylbiphenyl. The preferred diisopropyl aromatic compound is 1,4-diisopropylbenzene (p-diisopropylbenzene, p-DIPB) which is used in the manufacture of high performance polyesters. The p-DIPB is oxidized in the oxidation zone to its mono-and di-hydroperoxides which, in accordance with our invention, are converted to 1,4-phenylene-bis(acetate) and 4-isopropylphenyl acetate in the rearrangement-esterification zone.

The rearrangement reaction also is performed according to known procedures except that in our process it is carried out in the presence of acetic anhydride. As is well-known in the art, the rearrangement of the hydroperoxide compounds is accomplished by contacting the hydroperoxides with an acidic rearrangement catalyst which may be a mineral acid such as sulfuric, an organic sulfonic acid methanesulfonic or toluenesulfonic acid or an ion exchange resin such as a sulfonated styrene-divinylbenzene polymer. Other materials which may be used as the acidic rearrangement catalyst are described in Methoden Der Organischen Chemie (Houben-Weyl), Vol. VI/1c, Part 1, Georg Thieme Verlag Stuttgart (1976), p. 124. When a homogeneous acid catalyst is used, the crude product obtained from the rearrangement-esterification zone must be neutralized with a basic material prior to submitting the crude product to distillation step (3). Such neutralization is not necessary when the acidic material is heterogeneous, e.g., an acidic ion exchange resin, which can be separated from the crude product by filtration. An especially suitable acidic catalyst is Amberlyst 15, an acidic ion exchange resin available from Rohm and Haas Company and described in Rohm and Haas publication "Amber-Hi-Lites", No. 128, May, 1972. The use of Amberlyst 15 in the analogous rearrangement or decomposition of cumene hydroperoxide to phenol is described in Rohm and Haas publication "Amber-Hi-Lites", No. 135, July, 1973.

The rearrangement-esterification may occur over a wide temperature range, e.g., from about 0° to 150° C. although the temperature more commonly will be in the range of about 20° to 100° C. The preferred temperature range is between about 50° and 70° C. The rearrangement-esterification reactions are not affected to any significant degree by pressure and thus these reactions normally occur at ambient pressures. Although the use of subatmospheric or superatmospheric pressure is believed to give no significant improvement in the operation of the rearrangement-esterification zone, total pressures in the range of about 0.5 to 1.5 atmospheres can be used if desired. Acetic anhydride is fed to the rearrangement-esterification reactor at a rate which is sufficient to maintain a stoichiometric amount, preferably a stoichiometric excess, with respect to the hydroperoxide groups of the compounds contained in the oxidizer product. Excess acetic anhydride may be recovered as a by-product of distillation step (3) and returned to the rearrangement-esterification reactor along with fresh anhydride.

Distillation zone (3) can comprise any combination of distillation apparatus which will accomplish the above-stated objective. Typically, the distillation zone includes low boiler and high boiler distillation means, e.g., columns. The low boiler distillation means may be operated at temperatures over the range of about 200° to 260° C. and pressures (total) over the range of about 0.5 to 1.5 atmospheres. Acetone, acetic acid and acetic anhydride are the primary materials taken overhead from the low boiler column. The residue or underflow from the low boiler column is fed to the high boiler column, e.g., at a point slightly higher or lower than the mid-point of the column, which is operated over a temperature range of about 200° to 325° C. and a pressure range of about 0.2 to 1.5 atmospheres total pressure. The distillate taken overhead from the high boiler column is made up primarily of unreacted diisopropyl aromatic compound and intermediate isopropyl aromatic compound, both of which are recycled to the oxidation zone. The underflow consists primarily of the desired diacetate ester of the aromatic compound, e.g., p-phenylene-bis(diacetate), which may be further refined if desired. Alternatively, a vapor stream containing a higher concentration of the desired diacetate may be taken from the high boiler column at a point along the lower one-half of the column with high boiling impurities being removed from the base of the column. The various useful distillation temperatures and pressures are dictated by the boiling points, vapor pressures and other properties of the compounds fed to the distillation zone as well as desired production rates and economical considerations. The particular combination of operating conditions and design of the distillation apparatus may be readily determined by those skilled in the art.

In a specific embodiment of the present process, high yields of p-phenylene-bis(acetate) (hydroquinone diacetate) suitable for use in the manufacture of polyesters can be obtained is good production rates by:

(1) continuously feeding a mixture of p-DIPB and p-isopropylphenyl acetate and air to an oxidizer vessel operated at 50° to 120° C. and at an oxygen partial pressure of from about 0.2 to 3.0 atmospheres to form an oxidiation product comprising the mono- and di-hydroperoxides of DIPB, p-isopropylphenyl acetate hydroperoxide, unoxidized p-DIPB, unoxidized p-isopropylphenyl acetate and minor amounts of by-products;

(2) continuously feeding oxidation product and acetic anhydride to an agitated vessel containing an acidic catalyst and forming at a temperature of 40° to 80° C. a rearrangement-esterification product comprising p-phenylene-bis(diacetate), p-isopropylphenyl acetate, p-DIPB, acetone, acetic anhydride, acetic acid and minor amounts of by-products;

(3) continuously feeding rearrangement-esterification product to a low boiler unit (column) operating at a temperature over the range of 200° to 260° C. and at a total pressure over the range of 0.5 to 1.5 atmospheres to distill off a mixture containing primarily acetic anhydride, acetic acid and acetone and continuously feeding the residual material containing primarily p-phenylene-bis(diacetate), p-isopropylphenyl acetate and p-DIPB to a high boiler unit (product column) operating over a temperature of 200° to 325° C. and a total pressure over the range of 0.2 to 1.5 atmospheres to obtain a stream rich in p-phenylene-bis(acetate) product and a stream rich in p-isopropylphenyl acetate and p-DIPB; and (4) continuously recycling the mixture of p-DIPB and p-isopropylphenyl acetate to the oxidizer vessel.

In the above-described embodiment of our invention, the integration of the co-oxidation of p-DIPB and p-isopropylphenyl acetate, the rearrangement-esterification of all of the intermediate hydroperoxides, and an appropriately configured distillation train affords a process for the production of p-phenylene-bis(acetate) which is considerably simpler, more direct, less costly and much more efficient than first producing and isolating the aromtic diol (hydroquinone) and then esterifying it. A further significant advantage of our process over known methods is that it eliminates the need for isolating and purifying the dihydroperoxide of p-DIPB and, hence, the hazardous deposition of impact sensitive crystals of the dihydroperoxide is avoided.

Our novel process is further illustrated by the following example of the continuous production of p-phenylene-bis(diacetate).

EXAMPLE 1

To each of four columnar oxidation vessels at a point near the top is fed per hour 2260 pounds of p-DIPB (575 pounds fresh, 1685 pounds recycle) and 4550 pounds of p-isopropylphenyl acetate. Air is fed by means of a sparger near the bottom of the oxidizer at a rate of 1275 pounds per hour. Conditions within the oxidizer are 80° C. and approximately 7 atmospheres total pressure. The temperature is maintained by removing vapor from the top of the oxidizer and returning condensible material to the oxidizer. The conversion of the oxygen fed is approximately 75 percent. Crude oxidizer product is removed from the base of the oxidizer and fed to an agitated tank in which the rearrangement-esterification takes place.

The oxidizer product fed to the rearrangement-esterification reactor represents an hourly flow rate from each of the four oxidizers of 2325 pounds of p-DIPB monohydroperoxide, 350 pounds of p-DIPB dihydroperoxide and 2430 pounds of p-isopropylphenyl acetate hydroperoxide. The oxidizer product also contains a significant amount of other compounds comprising a major amount of unreacted p-DIPB and a minor amount of other oxygenated by-products, e.g., carbinols and ketones. Acetic anhydride also is fed to the rearrangement-esterification reactor at an hourly rate of 3163 pounds (2725 pounds fresh, 438 pounds recycle). A suspension or dispersion of Amberlyst 15 resin beads is maintained in the rearrangement-esterification reactor which is equipped with a screened filter leg through which liquid product, but not resin catalyst beads, is removed from the reactor.

The product from the rearrangement-esterification reactor is fed to the mid-point of a 70-tray still operated at 1 atmosphere (total pressure) and over a temperature range of 225° to 240° C. The stream taken overhead consists primarily of acetone, acetic acid and acetic anhydride which can be further separated by means of two distillation columns into by-products acetone and acetic acid and recycle acetic anhydride. The underflow from the low boiler column is fed to the mid-point of a second column containing 50 trays and operated at a pressure (total) of 0.5 to 1.0 atmosphere and a temperature over the range of 225° to 300° C. Unreacted p-DIPB and p-isopropylphenyl acetate are taken overhead and returned to the feed tank for the oxidizers. A product stream consisting essentially of p-phenylene-bis(diacetate) is removed at a point approximately one-fourth of the height of the still from the bottom. A high boiler stream is removed from the base of the still. The product stream is solidified to obtain p-phenylene-bis(acetate) of 95 percent purity at a rate of 2655 pounds per hour.

The chemistry involved in the first two steps of our novel continuous process is further illustrated by the following examples in which a mixture of p-DIPB and p-isopropylphenyl acetate is oxidized to a mixture of hydroperoxides which then is fed to a rearrangement-esterification zone in which the hydroperoxides are converted to hydroquinone diacetate and p-isopropylphenyl acetate. The apparatus used in the oxidation zone consisted of a glass bulb connected to an oxygen reservoir by flexible metal tubing. The p-DIPB, p-isopropylphenyl acetate, base (calcium hydroxide) and initiator (2-t-butylazo-2-cyanopropane) were placed in the glass bulb which was then pressurized with oxygen. The bulb was shaken mechanically in a constant temperature bath at 80° C. and consumption of oxygen noted by change of gauge pressure on the reservoir tank. The reported oxidation periods commenced shortly after the glass bulb containing the reactants had been agitated in the constant temperature bath. After a certain amount of oxygen had been absorbed, the bulb was detached from the metal tubing and the product-unconsumed reactant mixture was taken up in acetone and the resulting solution was filtered to remove the base. The oxidate solution was added over a period of about 60 minutes to a stirred mixture of Amberlyst 15 resin beads in acetic anhydride at room temperature and the resulting rearrangement-esterification mixture was stirred an additional 60 minutes after the addition of the oxidizer product was completed. Analytical techniques used were liquid chromatography and iodometric titration for hydroperoxides and gas chromatography for esters.

EXAMPLE 2

A mixture of p-DIPB (0.131 mol), p-isopropylphenyl acetate (0.143 mol), calcium hydroxide (0.21 g) and initiator (0.244 g) was oxidized for 395 minutes. The acetone solution of the oxidate containing p-DIPB dihydroperoxide (0.0032 mol), p-DIPB monohydroperoxide (0.0328 mol) and p-isopropylphenyl acetate hydroperoxide (0.024 mol) was added to a mixture of Amberlyst 15 resin beads (5.64 g) in acetic anhydride (42.13 g) and allowed to react to give a rearrangement-esterification product mixture which contained hydroquinone diacetate (0.0245 mol) and p-isopropylphenyl acetate (0.1641 mol).

EXAMPLE 3

A mixture of p-DIPB (0.0796 mol), p-isopropylphenyl acetate (0.1997 mol), calcium hydroxide (0.198 g) and initiator (0.2067 g) was oxidized for 535 minutes. The acetone solution of the oxidate containing p-DIPB dihydroperoxide (0.0026 mol), p-DIPB monohydroperoxide (0.0225 mol) and p-isopropylphenyl acetate hydroperoxide (0.0322 mol) was added to a mixture of Amberlyst 15 resin beads (6.02 g) in acetic anhydride (41.28 g) and allowed to react to give a rearrangement-esterification mixture which contained hydroquinone acetate (0.0384 mol) and p-isopropylphenyl acetate (0.2065 mol).

The invention has been described in detail with particular reference to preferred embodiments thereof, but it will be understood that variations and modifications can be effected within the spirit and scope of the invention. The invention is not limited to narrowly defined reaction conditions of temperature and pressure, feedstock feed rates, recycle rates, or type, design or mode of operation of reaction vessels, distillation equipment and the like. Those skilled in the art can readily determine those conditions and operating details which will give optimum results.

We claim:

1. A continuous process for the preparation of diacetate esters of aromatic diols which comprises the steps of:
   (1) contacting in an oxidation zone a feedstock comprising a diisopropyl aromatic compound and recycle isopropyl aromatic acetate with an oxygen-containing gas under hydroperoxide forming conditions of temperature and pressure to form a reaction mixture comprised of the mono- and di-hydroperoxides of the feedstock;
   (2) contacting in a rearrangement-esterification zone the reaction mixture formed in the oxidation zone with an acidic rearrangement catalyst and acetic anhydride under rearrangement-esterification conditions of temperature and pressure to form an ester mixture comprising the diacetate of the corresponding aromatic diol and the isopropyl aromatic acetate;
   (3) submitting the ester mixture obtained from the rearrangement-esterification zone to distillation to separate the diacetate compound from the acetate compound; and
   (4) recycling the acetate compound to the oxidation zone wherein the aromatic nucleus contains from 6 to 14 carbon atoms.

2. The process of claim 1 wherein the feedstock is a mixture of (a) diisopropylbenzene and isopropylphenyl acetate, (b) diisopropylnaphthalene and isopropylnaphthyl acetate or (c) diisopropylbiphenyl and isopropylbiphenyl acetate.

3. The process of claim 2 wherein the oxidation is carried out at about 50° to 120° C. and at an oxygen partial pressure of about 0.2 to 5.0 atmospheres and the rearrangement-esterification reaction is carried out at about 20° to 100° C.

4. The process of claim 2 wherein the oxidation is carried out at about 70° to 100° C. and at an oxygen partial pressure of about 0.2 to 3.0 atmospheres and the rearrangement-esterification reaction is carried out at about 50° to 70° C.

5. A continuous process for the preparation of p-phenylene-bis(acetate) which comprises the steps of:
   (1) contacting in an oxidation zone at a temperature of about 50° to 120° C. and at an oxygen partial pressure of about 0.2 to 5.0 atmospheres a feedstock comprising p-diisopropylbenzene and recycle p-isopropylphenyl acetate with an oxygen-containing gas to form a reaction mixture comprised of the mono- and di-hydroperoxides of p-diisopropylbenzene, p-isopropylphenyl acetate hydroperoxide, unoxidized p-diisopropyl benzene and unoxidized p-isopropylphenyl acetate;
   (2) contacting in a rearrangement-esterification zone at about 40° to 80° C. the reaction mixture formed in the oxidation zone with an acid catalyst and acetic anhydride to form an ester mixture comprising p-phenylenebis(acetate), p-isopropylphenyl acetate, p-diisopropylbenzene, acetic anhydride, acetic acid and acetone;
   (3) submitting the ester mixture obtained from the rearrangement esterification zone to a low boiler distillation unit operating at a temperature over the range of about 200° to 260° C. and over a total pressure range of about 0.5 to 1.5 atmospheres to distill off a mixture comprising primarily acetic anhydride, acetic acid and acetone, feeding the residual mixture comprising p-phenylenebis(acetate), p-isopropylphenyl acetate and p-diisopropylbenzene to a high boiler distillation unit operating at a temperature over the range of about 200° to 325° C. and a total pressure over the range of about 0.2 to 1.5 atmospheres to obtain a distillate comprising primarily p-diisopropylbenzene and p-isopropylphenyl acetate; and
   (4) recycling the distillate to the oxidation zone and recovering p-phenylenebis(acetate).

* * * * *